United States Patent
Schwenk et al.

(10) Patent No.: US 10,098,572 B2
(45) Date of Patent: Oct. 16, 2018

(54) METHOD FOR OPERATING A MONITORING SYSTEM

(75) Inventors: Marcus Schwenk, Stuttgart (DE); Alexander Dubielczyk, Stuttgart (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1020 days.

(21) Appl. No.: 13/384,244

(22) PCT Filed: Jul. 13, 2010

(86) PCT No.: PCT/IB2010/053192
§ 371 (c)(1),
(2), (4) Date: Jan. 16, 2012

(87) PCT Pub. No.: WO2011/010244
PCT Pub. Date: Jan. 27, 2011

(65) Prior Publication Data
US 2012/0123226 A1    May 17, 2012

(30) Foreign Application Priority Data
Jul. 20, 2009  (EP) .................... 09165889

(51) Int. Cl.
A61B 5/00    (2006.01)
A61B 5/11    (2006.01)
A61B 5/1455  (2006.01)

(52) U.S. Cl.
CPC .......... *A61B 5/1118* (2013.01); *A61B 5/1122* (2013.01); *A61B 5/1123* (2013.01); *A61B 5/14551* (2013.01); *A61B 5/721* (2013.01); *A61B 2560/0209* (2013.01); *A61B 2562/0219* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,860,751 | A * | 8/1989 | Callaghan | 607/16 |
| 5,718,235 | A * | 2/1998 | Golosarsky et al. | 600/515 |
| 6,093,151 | A * | 7/2000 | Shine et al. | 600/485 |
| 6,580,356 | B1 * | 6/2003 | Alt | B60R 25/23 340/10.41 |
| 7,245,965 | B1 * | 7/2007 | Pei et al. | 607/9 |
| 8,924,248 | B2 * | 12/2014 | Tropper | A61B 5/1118 463/36 |
| 2002/0002338 | A1 * | 1/2002 | Palma et al. | 600/485 |
| 2002/0103422 | A1 * | 8/2002 | Harder et al. | 600/300 |
| 2003/0028085 | A1 * | 2/2003 | Al-Ali | 600/323 |
| 2003/0134657 | A1 * | 7/2003 | Norta | G01S 5/02 455/550.1 |

(Continued)

FOREIGN PATENT DOCUMENTS

| | | | |
|---|---|---|---|
| EP | 0191404 A1 | 8/1986 | |
| EP | 1421896 A2 | 5/2004 | |

(Continued)

*Primary Examiner* — Michael Kahelin
*Assistant Examiner* — Shirley Jian

(57) ABSTRACT

For saving power in a monitoring system for monitoring physiological data of a patient, motion activity data of the patient is obtained and measurements of physiological data of the patient are initiated, only when the motion activity is both non-zero and below a selected threshold.

20 Claims, 1 Drawing Sheet

(56) References Cited

U.S. PATENT DOCUMENTS

| | | | |
|---|---|---|---|
| 2003/0214408 A1* | 11/2003 | Grajales | A61B 5/0002 340/573.1 |
| 2004/0030230 A1* | 2/2004 | Norris | 600/323 |
| 2004/0034293 A1 | 2/2004 | Kimball | |
| 2004/0054269 A1* | 3/2004 | Rantala et al. | 600/322 |
| 2004/0098060 A1* | 5/2004 | Ternes | 607/17 |
| 2004/0181133 A1* | 9/2004 | Al-Ali | 600/323 |
| 2005/0149136 A1* | 7/2005 | Siejko et al. | 607/17 |
| 2006/0149146 A1* | 7/2006 | Schmidt et al. | 600/372 |
| 2006/0161070 A1* | 7/2006 | Siejko et al. | 600/528 |
| 2006/0229520 A1* | 10/2006 | Yamashita et al. | 600/503 |
| 2006/0247732 A1* | 11/2006 | Wesselink | 607/46 |
| 2006/0247739 A1* | 11/2006 | Wahlstrand et al. | 607/62 |
| 2007/0021678 A1* | 1/2007 | Beck et al. | 600/510 |
| 2007/0270671 A1* | 11/2007 | Gal | 600/301 |
| 2007/0299323 A1* | 12/2007 | Arns et al. | 600/301 |
| 2008/0064936 A1* | 3/2008 | Al-Ali | 600/300 |
| 2008/0093838 A1* | 4/2008 | Tropper | A61B 5/1118 283/67 |
| 2008/0161713 A1* | 7/2008 | Leyde et al. | 600/544 |
| 2008/0183847 A1 | 7/2008 | Kontothanassis et al. | |
| 2008/0231449 A1* | 9/2008 | Moshfeghi | G01D 21/00 340/572.1 |
| 2008/0232604 A1* | 9/2008 | Dufresne | A61B 5/061 381/67 |
| 2009/0082639 A1* | 3/2009 | Pittman et al. | 600/300 |
| 2009/0171788 A1* | 7/2009 | Tropper | A61B 5/1118 705/14.61 |
| 2009/0312650 A1* | 12/2009 | Maile et al. | 600/486 |
| 2010/0131788 A1* | 5/2010 | Lo | G06F 1/3228 713/323 |
| 2010/0217533 A1* | 8/2010 | Nadkarni et al. | 702/19 |
| 2010/0312188 A1* | 12/2010 | Robertson et al. | 604/156 |
| 2011/0264164 A1* | 10/2011 | Christopherson et al. | 607/42 |
| 2012/0123226 A1* | 5/2012 | Schwenk | A61B 5/1118 600/301 |
| 2017/0095215 A1* | 4/2017 | Watson | A61B 5/7285 |
| 2017/0156662 A1* | 6/2017 | Goodall | A61B 5/4836 |
| 2017/0164876 A1* | 6/2017 | Hyde | G16H 50/30 |

FOREIGN PATENT DOCUMENTS

| | | |
|---|---|---|
| WO | 2004016170 A1 | 2/2004 |
| WO | 2008072168 A1 | 6/2008 |
| WO | 2008096241 A2 | 8/2008 |
| WO | 2009037612 A2 | 3/2009 |
| WO | 2009072024 A1 | 6/2009 |

* cited by examiner

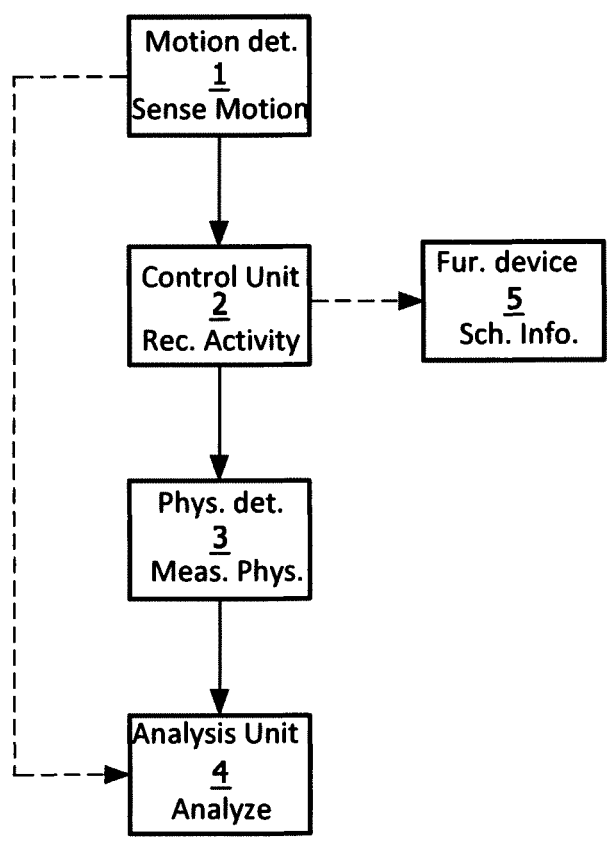

METHOD FOR OPERATING A MONITORING SYSTEM

FIELD OF THE INVENTION

The invention relates to the field of methods for operating monitoring systems for monitoring physiological data of a patient.

BACKGROUND OF THE INVENTION

Pulse oximeters determine the arterial oxygen saturation of hemoglobin (also called SpO2) and other hemodynamic parameters. The non invasive technique is widely used as a standard method for patient monitoring in the clinical environment. Typically oxygen saturation is continuously measured to monitor critical patients.

Document WO 2004/016170 A1 describes a technique to compensate for, or eliminate, motion-induced artifacts in patient-attached critical care monitoring instruments.

For the surveillance of non stationary patients, small and mobile monitoring system, in particular pulse oximeter devices, which are operated by small and lightweight batteries, are needed.

SUMMARY OF THE INVENTION

It is an object of the present invention to reduce the required electrical power of monitoring systems. This object is solved by the method according to the invention.

The method according to the invention is a method for operating a monitoring system for monitoring physiological data of a patient, comprising the steps:
 obtaining motion activity data of the patient, and
 initiating a measurement of physiological data of the patient, if the motion activity is non-zero and below a selected threshold.

Everyone who is monitored by any reason, for example an athlete, a healthy person, an elderly person, is in particular also understood as a patient. Examples for physiological data are pulse, blood oxygen saturation, blood pressure, temperature, electrical activity of the neurons (EEG), respiration rate, uterine contractions (Toco), fetal ultrasound and/or electrical activity of the myocardial muscle (ECG). A motion activity of zero is in particular understood as no motion or no detectable motion.

The required electrical power can be reduced by a non-continuous measurement, since the measuring device can consume less power when no measurement is performed.

Missing motion can indicate that the monitoring system is not attached to the patient. Therefore, the required electrical power can be reduced by not initiating the measurement of physiological data if the motion activity is zero.

Compared with periods of high motion activity, in which motion artifacts can necessitate the measurement of more data and more calculation effort, which both can raise the required electrical power, a monitoring system, for example a pulse oximeter, which is operated during a period of relatively low motion activity, can in particular record less data and/or apply less complex calculation methods or less complex filtering to separate the wanted physiological parameter from motion induced artifacts. Therefore, a measurement taken under low motion activity can be finished earlier and the required electrical power can be reduced while maintaining the measurement accuracy.

A reduction of the required electrical power can extend the operating time of a battery powering the monitoring system. Thereby, the battery can be less often replaced or charged, which can make the monitoring system more practical, more ecologically friendly and increases its usability as mobile device.

The motion activity data of the patient can in particular be obtained by sensing. Sensing motion activity can in particular include the acquisition of position, position change, orientation and orientation change. In particular, a measurement of physiological data of the patient can be initiated/activated/started, if the motion activity is non-zero or rather greater/above zero, and below a selected threshold.

The method is in particular a non-continuous or rather intermittent measurement method. In particular, single measurements or measurement cycles can be performed at predetermined points in time or on demand by a trigger, such as by a given threshold or for spot checking by the patient or physician (external trigger), followed by periods in which no measurements are performed.

In one embodiment of the present invention, an ongoing measurement of physiological data is shut down/deactivated/stopped, if the motion activity is above or equal to a selected threshold. Thus, the method can decide to shut down/stop an ongoing measurement, if current movement is likely to extend the needed measurement period.

When initiating the measurement, one or more electronic parts of the monitoring system, such as one or more electronic parts of a physiological data detector, for example a lamp and/or processor, one or more complete physiological data detectors, or one or more circuit components, can be switched on. Between the measurements, one or more electronic parts of the monitoring system, such as one or more electronic parts of a physiological data detectors, for example a lamp and/or processor, one or more complete physiological data detectors, or one or more circuit components, can be switched off or to stand-by-mode. Switching on or off or to stand-by-mode electronic parts can for example be effected by a superordinate unit, such as a central monitoring and/or controller unit, for example by connecting or interrupting the electrical power supply of the physiological data detector. Thereby further electrical power can be saved. Therefore, in one embodiment of the present invention, one or more electronic parts of the monitoring system, such as one or more electronic parts of a physiological data detector, for example a lamp and/or processor, one or more complete physiological data detectors, or one or more circuit components, are switched on, if the measurement of physiological data is initiated and/or one or more electronic parts of the monitoring system, such as one or more electronic parts of a physiological data detector, for example a lamp and/or processor, one or more complete physiological data detectors, or one or more circuit components, are switched off or to stand-by-mode, if the measurement of physiological data is shut down/stopped. Again, the required electrical power of the monitoring system can be reduced and the operating time of a battery powering the monitoring system can be further extended.

An ongoing measurement of physiological data can be stoppable within a configurable stopping window after the initiation/start of the measurement. For example, an ongoing measurement of physiological data is stopped within the configurable stopping window after the initiation/start of the measurement, if the motion activity is above or equal to a selected threshold.

The length of the stopping window can be chosen by the user or a connected system to set priority between power saving and equidistant intervals. Moreover, choosing the length of the stopping window can get automated to adapt to the current situation of the patient. The method can for example set higher priority to equidistant intervals, if the patient needs more attention. Thus, the length of the stopping window can be set automatically, in particular in a manner adapted to the current situation of the patient, or by a person, such as the patient, a physician, a nurse or a trainer, or by a connected system. By setting the length of the stopping window, the priority between power saving and equidistant intervals can be changed. For example, a higher priority to equidistant intervals can be advantageous, if the patient needs more attention. This can for example be achieved by a shorter length of the stopping window.

The method can allow to gather data in a certain periodicity, by using the fact that the points in time for a single measurement can be flexible within a schedule and without taking the measurements at exactly the preselected points in time. This in turn, can make the method suitable for low acuity monitoring of, for example non critical or mobile patients, which are free to move or exercise, such as patients in emergency waiting rooms, general ward, during rehabilitation in the clinical environment or at home.

By the method, the actual point in time to initiate/start a measurement or to shut down/stop an ongoing measurement of a monitoring system in intermittent mode, such as a pulse oximeter in intermittent mode, can be optimized. For example, the method can take information about the body movement and decide whether to alter the schedule for the next measurement. For example, a measurement can be scheduled earlier or later than its predetermined point, in particular depending on the characteristics and/or intensity of the observed motion artifacts and/or the patient's situation. For example, it can be aimed to start the measurement during a period with probable low motion artifacts. This can lead to a shorter measurement interval. Moreover, if a measurement is already started, the method can take information about the body movement and decide whether to shut down/stop the ongoing measurement or not. Stopping an ongoing measurement can be beneficial if the actual observed motion artifacts are likely to extend the needed measuring period. Therefore, in another embodiment of the present invention, there is a time schedule scheduling points in time for measurements of physiological data. In particular the method comprises or rather is based on a time schedule scheduling points in time for measurements of physiological data. The scheduled points in time for measurements of physiological data can be scheduled periodically or non-periodically or a mix of both. For example, the time schedule can comprise only a few, periodically or non-periodically scheduled points in time for measurements of physiological data per minute or per hour.

Instead of starting a measurement exactly at a predetermined point in time, the method can decide to delay or advance or remove the actual measurement or to add another measurement. For example, the method can advance or delay scheduled points in a configurable window enclosing the predetermined point. Therefore, in a further embodiment of the present invention, a scheduled point in time for a measurement of physiological data is alterable, in particular can be advanced or delayed, within a configurable alteration window enclosing the scheduled point.

The length of the alteration window can for example be chosen by the user or a connected system to set priority between power saving and equidistant intervals. Moreover, choosing the length of the alteration window can get automated to adapt to the current situation of the patient. For example, the method can set higher priority to equidistant intervals, if the patient needs more attention. Thus, in yet another embodiment of the present invention, the length of the alteration window is set automatically, in particular in a manner adapted to the current situation of the patient, or by a person, such as the patient, a physician, a nurse or a trainer, or by a connected system. By setting the length of the alteration window, the priority between power saving and equidistant intervals can be changed. For example, a higher priority to equidistant intervals can be advantageous, if the patient needs more attention. This can for example be achieved by a shorter length of the alteration window.

The method can for example decide to advance or add a scheduled point, if the current movement artifacts are low and a short measuring period is probable. Therefore, in another embodiment of the present invention, a scheduled point in time for a measurement of physiological data is advanced or added, if the motion activity is below a selected threshold.

During low movement the method can control the measurement to end earlier by recording less measured data samples. Thus, in a further embodiment of the present invention, a scheduled measurement of physiological data can be stopped earlier, if the motion activity is below a selected threshold. By this way, time for data capturing and electrical power can be saved while a specified accuracy can be maintained.

The method can also delay or remove a scheduled point if movement is likely to extend the measurement period. Thus, in yet another embodiment of the present invention, a scheduled point in time for a measurement of physiological data of the patient is delayed or removed, if the motion activity is above a selected threshold.

The method can also delay or remove a scheduled point, if absence of movement suggests that the measurement device is currently not applied to a patient. Hence, in another embodiment of the present invention, a scheduled point in time for a measurement of physiological data is delayed, if the motion activity is nil or, for example, close to nil.

From the motion activity characteristics, in particular the motion activity pattern, different motion situations can be classified. For example the motion situation "reading a book" could have long intervals with low motion activity, which are interrupted by short intervals with significant higher motion activity, when a page is turned over. The motion activity characteristics can for example be determined by counting the number, frequency and magnitude of movements, such as very strong, medium strong and weak motions. "Exercising on a home trainer" or "climbing stairs" (situation with fast and repetitive motion) and "sleeping" (situation with very low motion) could for example be different motion situations than "reading a book" (situation with low and regular motion). Preferably, the method provides an individual optimization of the measurement schedule of the different motion situations. For classifying motion situations optionally further data, such as respiration data, could be correlated with the motion parameters.

Preferably, the method comprises the step: analyzing the motion activity characteristics, in particular the motion activity pattern, for one or more motion situations. For example, the measurement of physiological data of the patient can be initiated, and for example subsequently switched off, at a point in time, which is estimated to have a low motion activity according to the analyzed motion characteristics and/or motion situation. For example, in the motion situation "reading a book" the measurement of physiological data of the patient could be initiated, and preferably subsequently switched off, within the long intervals with low motion activity between the short intervals for page turning.

The motion activity characteristics, in particular the motion activity pattern, of a patient can be measured, analyzed and stored, for example in a storing unit, during an initialization phase. For example, this initialization phase can be 24 hours long.

In another embodiment of the present invention, the method comprises the step of identifying motion situation by comparing the current motion activity characteristics, in particular the motion activity pattern, with one or more stored motion activity characteristics, in particular motion activity pattern.

In another embodiment of the present invention, the measurement of physiological data of the patient is initiated/started, if the current motion activity characteristic, in particular motion activity pattern, has a lower motion activity than a stored motion activity characteristic, in particular motion activity pattern, for this motion situation.

Furthermore, an ongoing measurement of physiological data can for example be shut down/stopped, if the motion situation suggests that another measurement, in particular an earlier measurement, is more likely to finish earlier and/or if the motion situation suggests that the measurement will take too long. In another embodiment of the present invention, an ongoing measurement of physiological data is shut down/stopped, if the current motion activity characteristic, in particular motion activity pattern, has a higher motion activity than a stored motion activity characteristic, in particular motion activity pattern, for this motion situation.

In another embodiment of the present invention, a scheduled point in time for a measurement of physiological data is advanced or added, if the current motion activity characteristic, in particular motion activity pattern, has a lower motion activity than a stored motion activity characteristic, in particular motion activity pattern, for this motion situation.

In another embodiment of the present invention, a scheduled measurement of physiological data is stopped earlier, if the current motion activity characteristic, in particular motion activity pattern, has a higher motion activity than a stored motion activity characteristic, in particular motion activity pattern, for this motion situation.

In another embodiment of the present invention, a scheduled point in time for a measurement of physiological data is delayed or removed, if the current motion activity characteristic, in particular motion activity pattern, has a higher motion activity than a stored motion activity characteristic, in particular motion activity pattern, for this motion situation.

The method can define the needed amount of data depending on the present movement artifacts. Thus, in a further embodiment of the present invention, the measured amount of physiological data is adapted to the motion activity, in particular the motion activity characteristics, for example the motion activity pattern.

In yet another embodiment of the present invention, the method further comprises the step of analyzing the measured physiological data. The method can define the depth and/or method set of analysis depending on the present movement artifacts. In particular; the depth and/or method set of analysis of the measured physiological data or the selection of mathematical or technical methods is adapted to the motion activity, in particular the motion activity characteristics, for example the motion activity pattern.

During low movement the method can control the data analysis to use less electrical power for computation by selecting less complex data processing or less complex mathematical or statistical methods. In particular, the complexity of the analysis is reduced if the motion activity is below a selected threshold.

In yet another embodiment of the present invention, the method further comprises the step of providing scheduling information to at least one further device, for example a mobile or a stationary device, in particular for changing the measurement schedule of the further device or for saving power of the further device or for synchronizing the measurements of at least two devices. Such an input can for example be used to start synchronous measurements or align interfering measurements on the schedule.

In general, different thresholds can be selected for several aspects of the method, such as for starting, stopping, advancing and delaying the measurement of the physiological data. However, the method can be simplified by selecting a small number or only one threshold for all aspects.

Another subject of the present invention is a monitoring system for monitoring physiological data of a patient, in particular for carrying out a method according to the invention, comprising a motion detector configured to sense motion activity of the patient, at least one physiological data detector configured to measure physiological data of the patient and a controller unit configured to receive motion activity data of the motion detector and to activate the physiological data detector to measure physiological data if the motion activity is non-zero and below a selected threshold.

This monitoring system can also have a reduced electrical power consumption.

In general, the motion detector and physiological data detector of the monitoring system can be integrated in the same device or in different devices.

Preferably, the controller unit is configured to deactivate the measuring physiological data detector, if the motion activity is above or equal to a selected threshold. In particular, the controller unit can be configured to switch on one or more electronic parts of a physiological data detector, for example a lamp and/or processor, one or more complete physiological data detectors, or one or more circuit components, if the measurement of physiological data is activated and/or to switch off or to stand-by-mode one or more electronic parts of a physiological data detector, for example a lamp and/or processor, one or more complete physiological data detectors, or one or more circuit components, if the measurement of physiological data is deactivated. The controller unit can for example be a superordinate unit, such as a central monitoring and/or controller unit. For example the controller unit can activate or rather deactivate the physiological data detector by connecting or interrupting the electrical power supply of the physiological data detector. Furthermore, the controller unit can be configured to deactivate the physiological data detector within a configurable stopping window after the start of the measurement. For example, the controller unit is configured to deactivate the physiological data detector within the configurable stopping window after the start of the measurement, if the motion activity is above or equal to a selected threshold. Preferably, the controller unit is configured to set the length of the stopping window automatically, in particular in a manner adapted to the current situation of the patient, or by a person, such as the patient, a physician, a nurse or a trainer, or by a connected system. By setting the length of the stopping window, the priority between power saving and equidistant intervals can be changed. For example, a higher priority to equidistant intervals is advantageous, if the patient needs more attention and can be achieved by a shorter length of the stopping window.

Preferably, the controller unit is configured to activate and/or deactivate the physiological data detector to measure physiological data according to a time schedule, such as a time schedule scheduling points in time for measurements of physiological data. The scheduled points in time for measurements of physiological data can thereby be scheduled periodically or non-periodically. More preferably, the controller unit is configured to alter, in particular to advance or delay or add or remove, a scheduled point in time for a measurement of physiological data, for example within a configurable alteration window enclosing the scheduled point. Preferably, the controller unit is configured to configure the length of the alteration window automatically, in particular in a manner adapted to the current situation of the patient, or by a person, such as the patient, a physician, a nurse or a trainer, or by a connected system. By setting the length of the alteration window, the priority between power saving and equidistant intervals can be changed. For example, a higher priority to equidistant intervals can be advantageous, if the patient needs more attention and can be achieved by a shorter length of the alteration window.

Even more preferably, the controller unit is configured to advance or add a scheduled point in time for a measurement of physiological data, if the motion activity is below a selected threshold, and/or to stop a scheduled measurement of physiological data earlier, if the motion activity is below a selected threshold, and/or to delay or remove a scheduled point in time for a measurement of physiological data, if the motion activity is above or equal to a selected threshold, and/or to delay or remove a scheduled point in time for a measurement of physiological data, if the motion activity is nil or, for example, close to nil.

The controller unit can be configured to analyze the motion activity characteristics, in particular the motion activity pattern, for one or more motion situations. Furthermore, the controller unit can be configured to initiate, and for example subsequently switch off, the measurement of physiological data of the patient at a point in time, which is estimated to have a low motion activity according to the analyzed motion characteristics and/or motion situation. Moreover, the controller unit can be configured to measure, analyze and store, for example in a storing unit, the motion activity characteristics, in particular the motion activity pattern, of a patient during an initialization phase. Further on, the controller unit can be configured to identify a motion situation by comparing the current motion activity characteristics, in particular the motion activity pattern, with one or more stored motion activity characteristics, in particular motion activity pattern. Additionally, the controller unit can be configured to initiate/start the measurement of physiological data of the patient, if the current motion activity characteristic, in particular motion activity pattern, has a lower motion activity than a stored motion activity characteristic, in particular motion activity pattern, for this motion situation. Furthermore, the controller unit can be configured to shut down/stop an ongoing measurement of physiological data, if the current motion activity characteristic, in particular motion activity pattern, has a higher motion activity than a stored motion activity characteristic, in particular motion activity pattern, for this motion situation. Moreover, the controller unit can be configured to advance or add a scheduled point in time for a measurement of physiological data, if the current motion activity characteristic, in particular motion activity pattern, has a lower motion activity than a stored motion activity characteristic, in particular motion activity pattern, for this motion situation. Further on, the controller unit can be configured to stop a scheduled measurement of physiological data earlier, if the current motion activity characteristic, in particular motion activity pattern, has a higher motion activity than a stored motion activity characteristic, in particular motion activity pattern, for this motion situation. In addition, the controller unit can be configured to delay or remove a scheduled point in time for a measurement of physiological data, if the current motion activity characteristic, in particular motion activity pattern, has a higher motion activity than a stored motion activity characteristic, in particular motion activity pattern, for this motion situation.

Most preferably, the controller unit is configured to adapt the amount of physiological data measured by the physiological data detector to the motion activity sensed by the motion detector.

Furthermore, the monitoring system can comprise an analysis unit configured to analyze the measured physiological data. Preferably, the analysis unit is configured to adapt the depth and/or method set of analysis of the measured physiological data or the selection of mathematical or technical methods to the motion activity, in particular the motion activity characteristics, for example the motion activity pattern. For example, the analysis unit can be configured to reduce the complexity of the analysis if the motion activity is below a selected threshold.

Moreover, the motion detector, the physiological data detector, the controller unit and/or the analysis unit, in particular the controller unit, can be configured to provide scheduling information to at least one further device, for example a mobile or a stationary device, in particular for changing the measurement schedule of the further device or for saving power of the further device or for synchronizing the measurements of at least two devices.

The motion detector can be configured to acquire position, position change, orientation and/or orientation change data.

The motion detector can for example be a micro electrical mechanical system (MEMS), for example based on a cantilever beam accelerometer, a heat transfer accelerometer, a surface acoustic wave accelerometer, a laser accelerometer or a gyroscopic accelerometer.

The motion detector can also be a device which derives movement information indirectly by analyzing suitable patient parameters.

Moreover, the motion detector can be based on a positioning system, for example locating the position of the patient in a room or building and deriving movement information from positioning changing.

The motion detector can be a component comprised, in particular integrated, in the monitoring system, in particular in the physiological data detector, for example attachable to the patient or introducible into the patient.

However, the motion detector can also be a component comprised in a separate device having a data connection to the monitoring system, in particular the controller unit and/or the physiological data detector and possibly to other measurement devices, for example attachable to the patient or introducible into the patient. The connection can thereby for example be realized by cable or radio transmission. The second device can thereby be a device, for example a mobile device, which is attachable to the patient or introducible into the patient. However, the second device can also be a stationary device. For example the second device can be a device comprising a motion sensor with a positioning system, which derives movement information from positioning changing. The second device can also comprise a motion sensor with a camera, which derives movement information by observing the patient.

Preferably, the monitoring system, in particular the physiological data detector, is battery powered. The physiological data detector can for example be selected from the group consisting of pulse oximeter, none invasive blood pressure detector (NIBP), temperature sensor, electroencephalograph (EEG), respiration rate detector, uterine contraction detector, fetal ultrasound detector and electrocardiograph (ECG). Preferably, the physiological data detector is a pulse oximeter.

A further subject of the present invention is a computer program enabling a processor to carry out the method according to the invention. A computer program may be stored/distributed on a suitable medium, such as an optical storage medium or a solid-state medium supplied together with or as part of other hardware, but may also be distributed in other forms, such as via the Internet or other wired or wireless telecommunication systems.

Yet another subject of the present invention is the use of the method according to the invention and/or of the monitoring system according to the invention and/or of the computer program according to the invention in a patient monitor, in particular for low acuity care, for example for taking vital signs from a mobile patient, for example for emergency waiting rooms and/or for general ward and/or for rehabilitation and/or for home healthcare and/or for elderly care and/or for physical training, such as in a pulse oximeter, in particular for low acuity care, for example for taking vital signs from a mobile patient, for example for emergency waiting rooms and/or for general ward and/or for rehabilitation and/or for home healthcare and/or for elderly care and/or for physical training, in a none invasive blood pressure detector (NIBP), in particular for low acuity care, for example for taking vital signs from a mobile patient, for example for emergency waiting rooms and/or for general ward and/or for rehabilitation and/or for home healthcare and/or for elderly care and/or for physical training, in a temperature sensor, in particular for low acuity care, for example for taking vital signs from a mobile patient, for example for emergency waiting rooms and/or for general ward and/or for rehabilitation and/or for home healthcare and/or for elderly care and/or for physical training, in an electroencephalograph (EEG), in particular for low acuity care, for example for taking vital signs from a mobile patient, for example for emergency waiting rooms and/or for general ward and/or for rehabilitation and/or for home healthcare and/or for elderly care and/or for physical training, in a respiration rate detector, in particular for low acuity care, for example for taking vital signs from a mobile patient, for example for emergency waiting rooms and/or for general ward and/or for rehabilitation and/or for home healthcare and/or for elderly care and/or for physical training, in an uterine contraction detector, in particular for low acuity care, for example for taking vital signs from a mobile patient, for example for emergency waiting rooms and/or for general ward and/or for rehabilitation and/or for home healthcare and/or for elderly care and/or for physical training, in a fetal ultrasound detector, in particular for low acuity care, for example for taking vital signs from a mobile patient, for example for emergency waiting rooms and/or for general ward and/or for rehabilitation and/or for home healthcare and/or for elderly care and/or for physical training, and/or in an electrocardiograph (ECG), in particular for low acuity care, for example for taking vital signs from a mobile patient, for example for emergency waiting rooms and/or for general ward and/or for rehabilitation and/or for home healthcare and/or for elderly care and/or for physical training

BRIEF DESCRIPTION OF THE DRAWING

Additional details, features, characteristics and advantages of the object of the invention are disclosed in the subclaims, the FIGURE and the following description of the respective FIGURE, which—in an exemplary fashion—shows an embodiment of a method and monitoring system according to the invention.

FIG. 1 is a flow chart of an embodiment of the method according to the invention performed with an embodiment of the monitoring system according to the invention.

DETAILED DESCRIPTION

The invention will be further understood by the following example which—in a merely illustrative fashion—shows a flow chart of an embodiment of the method according to the invention performed with an embodiment of the monitoring system according to the invention.

FIG. 1 shows an embodiment of the monitoring system according to the invention, which comprises a motion detector 1, which is configured to sense motion activity of a patient, a physiological data detector 3, which is configured to measure physiological data of the patient, an analysis unit 4, which is configured to analyze the measured physiological data and a controller unit 2. FIG. 1 shows that the controller unit 2 is configured to receive motion activity data of the motion detector 1 and to activate the physiological data detector 3. According to the invention, the physiological data detector 3 is activated to measure physiological data if the motion activity sensed by the motion detector 1 is non-zero and below a selected threshold. Furthermore, FIG. 1 shows that the analysis unit 4 is configured to adapt the depth and/or method set of analysis of the physiological data to the motion activity sensed by and received from the motion detector 1. Moreover, FIG. 1 shows that the controller unit 2 is configured to provide scheduling information to a further mobile or a stationary device 5, in particular for changing the measurement schedule of the further device 5 or for saving power of the further device 5 or for synchronizing the measurements of the devices 1, 2, 3, 4, 5.

While the invention has been illustrated and described in detail in the drawings and foregoing description, such illustration and description are to be considered illustrative or exemplary and not restrictive; the invention is not limited to the disclosed embodiments. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. The mere fact that certain measures are recited in mutually different dependent claims does not indicate that a combination of these measures cannot be used to advantage. In the claims, the word "comprising" does not exclude other elements or steps, and the indefinite article "a" or "an" does not exclude a plurality. Any reference signs in the claims should not be construed as limiting the scope.

The invention claimed is:

1. A method for operating a monitoring system for monitoring physiological data of a patient, comprising:
   with non-invasive motion detector removably mounted to the patient, obtaining motion activity data indicative of patient movement;
   with an analysis unit, analyzing the motion activity data to determine whether motion activity is both non-zero and below a selected threshold;
   activating a non-invasive physiological detector that is removably mounted to the patient with power from a battery to acquire cardiac data of the patient only when the motion activity is both non-zero and below the selected threshold; and
   during an ongoing measurement of the cardiac data, in response to the motion activity increasing above or equal to the selected threshold, deactivating the physiological detector and stopping the acquisition of the cardiac data.

2. The method according to claim 1, further including:
   scheduling points in time for the physiological detector to acquire the cardiac data;
   in response to the motion activity exceeding the selected threshold advancing, deferring, or skipping one or more of the scheduled points in time; and
   in response to the motion activity being zero, advancing, deferring, or skipping one or more of the scheduled points in time.

3. The method according to claim 2, wherein at least one of the scheduled point in time for the acquisition of the cardiac data is alterable only within a configurable acquisition window enclosing the scheduled point in time.

4. The method according to claim 1, wherein a duration of the acquisition of the cardiac data is altered in accordance with the motion activity data.

5. The method according to claim 1, wherein obtaining the motion activity data includes obtaining a motion activity pattern characteristic of the motion activity pattern; and
   wherein analyzing the motion activity data includes: analyzing the motion activity pattern.

6. The method according to claim 1, further including:
   analyzing the acquired physiological data, wherein a method of analyzing the measured physiological data includes selecting an analysis algorithm from a plurality of analysis algorithms in accordance with the motion activity, wherein the algorithms require differing amounts of computing power and are susceptible to different levels of motion artifacting.

7. The method according to claim 1, further including:
   providing scheduling information to at least one device.

8. A non-transitory computer readable medium storing a computer program configured to control a processor to carry out the method of claim 1.

9. The method according to claim 1, further including:
   deactivating the physiological detector and stopping the acquisition of the cardiac data by prohibiting power from the battery from being transmitted to the non-invasive physiological detector.

10. A method for operating a monitoring system for monitoring physiological data of a patient, comprising:
    with a motion detector, obtaining motion activity data indicative of patient movement;
    activating a physiological detector with power from a battery to acquire physiological data of the patient at scheduled points in time;
    shortening a scheduled acquisition of physiological data, in response to the motion activity being non-zero and below the selected threshold at a first one of the scheduled points in time,
    delaying or removing one of the scheduled points in time for the acquisition of physiological data in response to the motion activity being above or equal to the selected threshold at a second one of the scheduled points in time, and
    delaying or removing one of the scheduled points in time for the acquisition of physiological data in response to the motion activity being nil at a third one of the scheduled points in time.

11. A method for operating a monitoring system for monitoring physiological data of a patient, comprising:
    with a motion detector, obtaining a patient motion activity pattern indicative of patient movement;
    with an analysis unit, analyzing the patient motion activity pattern characteristics by comparing the patient motion activity pattern with selected pattern characteristics to project a point in time when the patient motion activity will be both non-zero and below a selected threshold, and
    activating a physiological detector with power from a battery to acquire the physiological data at the projected point in time.

12. A monitoring system for monitoring physiological data of a patient, comprising:
    a non-invasive motion detector configured to be removably attached to a patient to sense motion activity of the patient;
    at least one non-invasive physiological data detector configured to be removably attached to a patient to measure physiological data of the patient; and
    a controller configured to:
    receive the sensed motion activity from the motion detector;
    analyze the received motion activity to determine whether the motion activity is both below a selected threshold and non-zero;
    activate the physiological data detector to measure physiological data only if the motion activity is non-zero and below the selected threshold; and
    during an ongoing measurement of the cardiac data, in response to the motion activity increasing above or equal to the selected threshold, deactivating the physiological detector and stopping the acquisition of the cardiac data.

13. The system according to claim 12, wherein the controller includes a processor and is further configured to:
    schedule points in time for the at least one physiological data detector to measure the physiological data based on analyzing the received motion activity; and
    delay or remove one of the scheduled points in time for a measurement of physiological data in response to the motion activity being nil.

14. The system according to claim 12, wherein the controller is further configured to:
    adjust an amount of the physiological data measured in accordance with the sensed motion activity.

15. A system for monitoring physiological data of a patient, comprising:

a non-invasive motion detector configured to sense motion activity of the patient;

at least one non-invasive physiological data detector configured to measure physiological data of the patient;

a processor configured to:

receive the sensed motion activity of the motion detector, activate the physiological data detector to measure physiological data if the motion activity is non-zero and below a selected threshold, select one of a plurality of analysis methods for analyzing the measured physiological activity, the plurality of analysis methods consuming varying levels of power and being susceptible to difference levels of motion artifacts, the one of the analysis methods being selected based on power consumption and a level of the sensed motion activity to lower both motion artifacts in the analyzed physiological data and power consumption.

16. A battery powered monitoring system for monitoring physiological data of a patient comprising:

a motion detector configured to sense motion activity of the patient;

at least one physiological data detector configured to measure physiological data of the patient; and a processor configured to:

receive the sensed motion activity from the motion detector;

analyze the received motion activity;

not activate the physiological data detector to initiate a measurement of the physiological data when the sensed motion activity is nil to preserve the battery life;

not activate the physiological data detector when the sensed motion activity meets or exceeds a threshold to preserve battery life;

activate the physiological data detector to make a measurement of the physiological data during times in which the sensed motion activity is between nil and the threshold;

adjust an amount of the physiological data measured when the physiological data detector is active based on the analysis of the sensed motion; and during an ongoing measurement of the cardiac data, in response to the motion activity increasing above or equal to the selected threshold, deactivating the physiological detector and stopping the acquisition of the cardiac data.

17. The system according to claim 16, wherein the processor is configured to analyze the motion activity by:

determining a pattern of the sensed motion activity; and performing a pattern analysis on the determined pattern.

18. The system according to claim 17, wherein the pattern analysis includes comparing the motion activity pattern with preselected pattern characteristics to determine whether the motion activity is nil or above the threshold.

19. The system according to claim 16, further including:

a memory configured to store a plurality of physiological data analysis algorithms, the algorithms using different amounts of battery power and having different susceptibility to motion artifacts;

wherein the processor is configured to select among the algorithms based on the analyzed motion activity to select an algorithm which minimizes motion artifacts and battery power usage.

20. The system according to claim 16, wherein the motion detector is non-invasive and the physiological data detector is a non-invasive heart monitor.

* * * * *